(12) United States Patent
DiPalma (10) Patent No.: US 6,413,338 B1
(45) Date of Patent: *Jul. 2, 2002

(54) METHOD FOR FORMING AN ABSORBENT STRUCTURE HAVING VERTICALLY ORIENTATED FLOW REGULATING WALLS

(75) Inventor: Joseph DiPalma, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/396,646

(22) Filed: Sep. 15, 1999

(51) Int. Cl.⁷ .......................... A61F 13/15; B32B 31/00
(52) U.S. Cl. ...................... 156/73.1; 156/253; 156/256; 156/264; 604/385.23; 604/385.01
(58) Field of Search ................. 156/73.1, 253, 156/256, 264, 263, 267, 269, 270; 604/385.23, 385.01

(56) References Cited

U.S. PATENT DOCUMENTS

| | | | |
|---|---|---|---|
| 3,668,054 A | 6/1972 | Stumpf | 428/152 |
| 3,838,694 A | 10/1974 | Mesek | 128/287 |
| 3,993,820 A | 11/1976 | Repke | 428/167 |
| 4,015,604 A | 4/1977 | Csillag | 128/287 |
| 4,100,324 A | 7/1978 | Anderson et al. | 428/288 |
| 4,443,512 A | 4/1984 | Delvaux | 428/162 |
| 4,467,012 A | 8/1984 | Pedersen et al. | 428/248 |
| 4,616,644 A | 10/1986 | Saferstein et al. | 128/156 |
| 4,627,848 A | 12/1986 | Lassen et al. | 604/370 |
| RE32,649 E | 4/1988 | Brandt et al. | 604/358 |
| 4,798,603 A | 1/1989 | Meyer et al. | 604/378 |
| 4,908,026 A | 3/1990 | Sukiennik et al. | 604/378 |
| 5,104,396 A | 4/1992 | Oatley et al. | 604/379 |
| 5,151,091 A | 9/1992 | Glaug et al. | 604/385.1 |
| 5,248,309 A | 9/1993 | Serbiak et al. | 604/368 |
| 5,336,552 A | 8/1994 | Strack et al. | 428/224 |
| 5,360,504 A | 11/1994 | Fell et al. | 156/247 |
| 5,364,382 A | 11/1994 | Latimer et al. | 604/378 |
| 5,399,175 A | 3/1995 | Glaug et al. | 604/385.1 |
| 5,401,267 A | 3/1995 | Couture-Dorschner et al. | 604/384 |
| 5,490,846 A | 2/1996 | Ellis et al. | 604/366 |
| 5,506,277 A | 4/1996 | Griesbach, III | 521/84.1 |
| 5,545,156 A | 8/1996 | DiPalma et al. | 604/385.1 |
| 5,613,962 A | 3/1997 | Kenmochi et al. | 604/378 |
| 5,643,240 A | 7/1997 | Jackson et al. | 604/378 |
| 5,649,916 A | 7/1997 | DiPalma et al. | 604/378 |
| 5,656,361 A | 8/1997 | Vogt et al. | 428/198 |
| 5,762,642 A | 6/1998 | Coles et al. | 604/378 |
| 5,807,365 A | 9/1998 | Luceri | 604/367 |
| 5,807,367 A | 9/1998 | Dilnik et al. | 604/367 |
| 5,843,063 A | 12/1998 | Anderson et al. | 604/378 |
| 5,846,231 A | 12/1998 | Fujioka et al. | 604/380 |
| 5,853,402 A | 12/1998 | Faulks et al. | 604/378 |
| 5,865,824 A | 2/1999 | Chen et al. | 604/378 |
| 5,869,171 A | 2/1999 | Shiveley et al. | 428/304.4 |
| 5,879,343 A | 3/1999 | Dodge et al. | 604/378 |
| 5,891,118 A | 4/1999 | Toyoshima et al. | 604/366 |
| 6,264,776 B1 * | 7/2001 | DiPalma | 156/73.1 |

FOREIGN PATENT DOCUMENTS

| | | |
|---|---|---|
| EP | 159 671 | 10/1985 |
| EP | 339461 | 11/1989 |
| EP | 366 079 | 5/1990 |
| EP | 586 936 | 3/1994 |
| WO | 98/56326 | 12/1998 |
| WO | 99/32165 | 7/1999 |

* cited by examiner

*Primary Examiner*—Linda Gray
(74) *Attorney, Agent, or Firm*—Pauley Petersen Kinne & Erickson (57) ABSTRACT

A method for forming an absorbent structure is provided wherein a fluid conveyance barrier member of preselected permeability is adjacently disposed between first and second absorbent members with the barrier member and the first and second absorbent members orientated such as to have a specifically desired ratio of horizontal width to vertical height.

29 Claims, 6 Drawing Sheets

METHOD FOR FORMING AN ABSORBENT STRUCTURE HAVING VERTICALLY ORIENTATED FLOW REGULATING WALLS

FIELD OF THE INVENTION

This invention relates generally to absorbent articles for absorbing body fluids and exudates. More particularly, the present invention relates to a method for forming absorbent pad assemblies and associated absorbent articles having improved leak prevention and/or fluid flow control.

BACKGROUND OF THE INVENTION

A wide variety of types of structures are known in the art for use in or as absorbent articles, particularly disposable absorbent articles, used to collect various body fluids and exudates. Commercial absorbent articles include diapers, adult incontinence products, sanitary napkins and bandages. Disposable products of this type generally comprise components for receiving, absorbing and retaining fluids. Typically, the components of such articles include a liquid permeable topsheet, an absorbent core and a liquid impermeable backsheet.

The components of typical absorbent articles are commonly plied or arranged in a horizontal fashion with a major planar surface facing the fluid intake area, e.g., the body of the wearer. In such absorbent articles, the nature or make-up of the fluid communicating therethrough can and typically will change as such fluid traverses though the horizontal ply or plies. Thus, such absorbent articles may experience undesirable horizontal dependency between components. Further, the fibers which customarily make-up the absorbent core are often orientated randomly with fibers within a mat in a lateral neighboring arrangement such that the fluid intake typically wicks in a radial fashion or pattern.

One of the main objectives in the development of absorbent articles is to increase, improve or maximize utilization of the absorbent capacity of the article. In general, products of the type described above typically distribute liquids deposited on the topsheet in a circular pattern. Since such structures generally have a length that exceeds their width, this may undesirably result in the fluids, e.g., exudates, reaching the longitudinal side edges of the absorbent article prior to the desirable utilization of the absorbent capacity at the end regions of the absorbent article. As will be appreciated, such occurrence may undesirably increase the possibility or likelihood of leakage from the sides of the article despite the availability of unutilized or underutilized absorbent capacity in the end regions of the absorbent article.

Moreover, such absorbent articles can and may be subjected to a wide range of conditions and applications such as due to factors inherent or related to the environment in which the article is utilized. Thus, the fluids which may need to be absorbed thereby may vary in properties or parameters such as including flow rate as well as form, phase or composition. For example, exudates may be multiphasic and heterogeneous, such as in the case of menses which may include red blood cells, mucin, plasma and tissue debris, for example.

Sanitary napkins (also referred to as catamenial pads), feminine pads, overnight pads, panty liners and panty shields are designed to be worn by a female to absorb menses and other body fluids discharged before, during and after a menstrual period. Sanitary napkins are external devices which are designed to be aligned approximate the pudendum region of a human body and are generally held in position by being adhesively or mechanically attached to an undergarment. Sanitary napkins also typically differ from panty liners and panty shields in several notable ways. Sanitary napkins are generally larger in size and have a more defined 3-dimensional configuration, are thicker in caliper and have a greater fluid capacity than panty liners or panty shields.

In view of the desire to provide increased comfort to the wearer and to minimize the appearance of the presence of such absorbent articles there is an ongoing demand and need for smaller or less bulky absorbent articles. Thus, there is a need and a demand for improved absorbent pad assemblies and absorbent articles such as may result in more complete utilization of the absorbent capacity thereof and such as may more effectively and efficiently respond to the possibly wide range of operating and performance conditions to which such assemblies and articles can be exposed. More particularly, there is a need and a demand for absorbent pad assemblies and absorbent articles which have improved control or management of fluid flow in association therewith.

SUMMARY OF THE INVENTION

A general object of the invention is to provide a method for forming absorbent structures such as either or both an improved absorbent pad assembly and absorbent article.

A more specific objective of the invention is to overcome one or more of the problems described above.

The general object of the invention can be attained, at least in part, through a method involving adjacently disposing at least a first generally planar fluid conveyance barrier member of preselected permeability between at least first and second absorbent members and orientating the adjacently disposed barrier member and first and second absorbent members wherein each of the first and second absorbent members has a ratio of horizontal width to vertical height of no more than about 10:1.

The prior art generally fails to provide absorbent pad assemblies and absorbent articles which make as complete or fall utilization of the absorbent capacity thereof as may be desired. The prior art also generally fails to provide absorbent pad assemblies and absorbent articles which can respond to the possibly wide range of operating and performance conditions to which such assemblies and articles can be exposed and to do so in an as effective and efficient a manner as may be desired.

The invention further comprehends a method for forming an absorbent pad assembly. In accordance with one preferred embodiment of the invention, such a method involves horizontally layering at least a first generally planar fluid conveyance barrier member of preselected permeability between first and second absorbent members and vertically reorientating the horizontally layered barrier member and first and second absorbent members.

In accordance with another embodiment, the invention still further comprehends a method for improving the fluid management by an absorbent article which includes a liquid pervious cover, a liquid impervious backsheet and an absorbent pad assembly disposed between the cover and the backsheet. The method involves the utilization of an absorbent pad assembly including a first generally planar fluid conveyance barrier member having a preselected permeability interposed between a pair of absorbent members generally perpendicularly disposed relative to the contact surface. As described in greater detail below, one particular form of such an absorbent article is a sanitary napkin.

Another aspect of the invention relates to specific absorbent structures. One such absorbent structure is a specific absorbent pad assembly which includes at least a first generally planar fluid conveyance barrier member of preselected permeability interposed between first and second vertically orientated absorbent members.

Another specific absorbent structure in accordance with such aspect of the invention has a contact surface and includes an absorbent pad assembly which includes at least first and second generally planar fluid conveyance barrier members. Each of the barrier members has a preselected permeability and is interposed between a pair of absorbent members which are generally perpendicularly disposed relative to the contact surface.

As used herein, references to "absorbent article(s)" are to be understood to refer to products such as diapers, sanitary napkins, training pants, incontinent garments, overnight pads, panty liners, under arm shields and the like, which are used to absorb body fluids and exudates, such as urine, menses, blood, perspiration and other excrements discharged by the body.

Further, references herein to absorbent members as being "vertically orientated" are to be understood to refer to the general disposition of the member and are in general reference relative to the body contacting surface or face of the absorbent article itself. In general, vertically orientated absorbent members are to be understood as having a ratio of horizontal width to vertical height of no more than about 10:1, preferably no more than about 5:1 and, more preferably about 1:1 or less.

References herein to adjacent absorbent members as being "noncontinuous" are to be understood to refer to such adjacent absorbent members as forming or having a surface interface therebetween. As will be appreciated, such a surface interface may, in practice, serve to hinder, prevent or avoid fluid passage between or from one to another of the adjacent absorbent members. As will be appreciated and as described in greater detail below, adjacent absorbent members will preferably differ in one or more property or characteristic such as chemical composition or construction such as fiber orientation or thickness, for example. Other effective properties or characteristics by which adjacent absorbent members may differ will be apparent to those skilled in the art and guided by the teachings herein provided.

References herein to adjacent absorbent members as forming a "surface interface" therebetween are to be understood as referring to the formation between adjacent members of a surface at which the adjacent members contact or are in proximity to each other.

References herein to "contact surface" are to be understood as referring to that surface of the absorbent member, pad assembly, article or the like with which the fluid to be absorbed initially contacts.

Other objects and advantages will be apparent to those skilled in the art from the following detailed description taken in conjunction with the appended claims and drawings.

DETAILED DESCRIPTION OF THE PRESENTLY PREFERRED EMBODIMENTS

The present invention, as is described in more detail below, provides an improved absorbent pad assembly and absorbent article as well as a method of forming such absorbent products.

Figure 1:
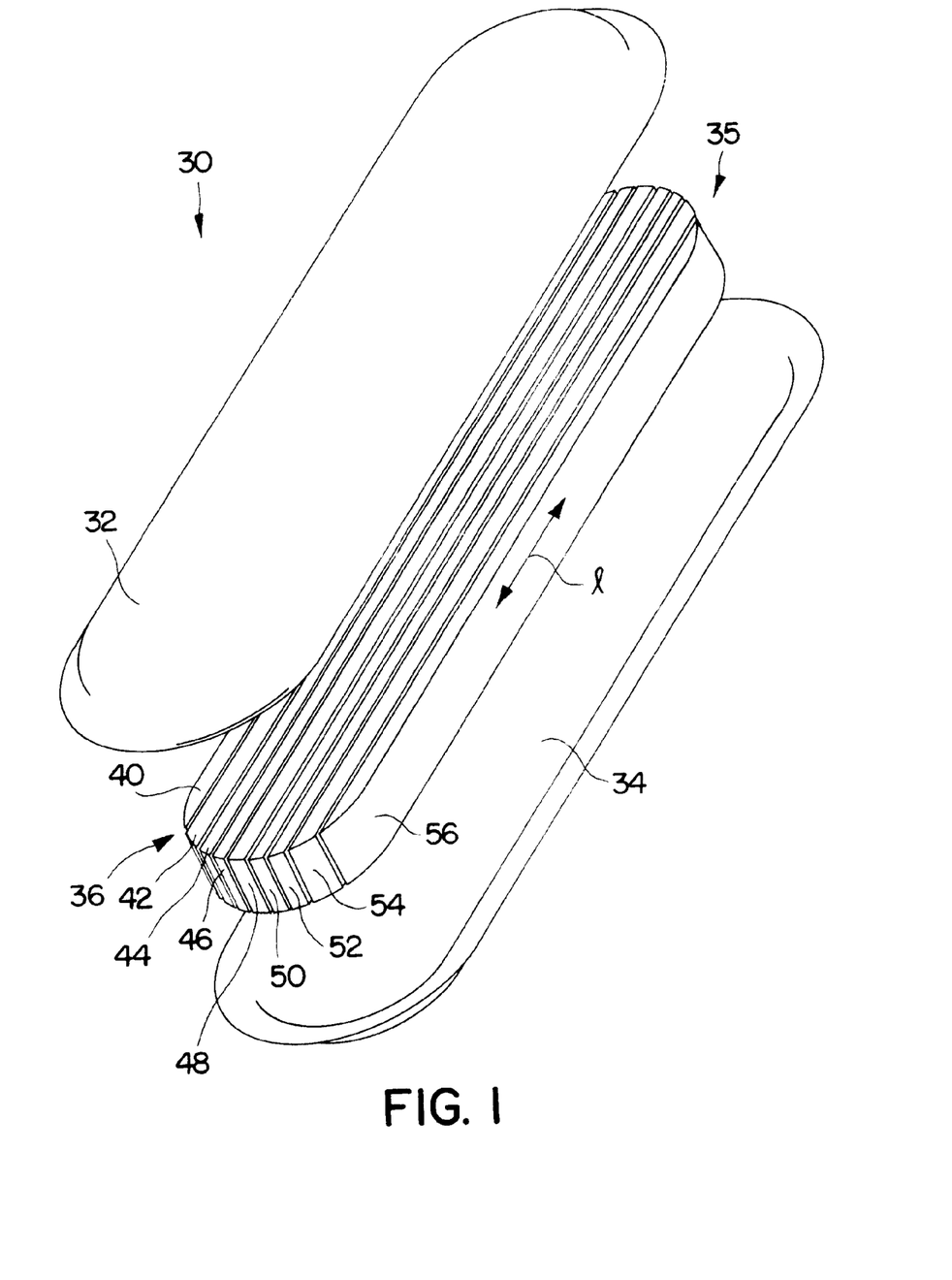
FIG. 1 is an exploded perspective view schematic of an absorbent article having a pad assembly in accordance with one preferred embodiment of the invention.
Figure 2:
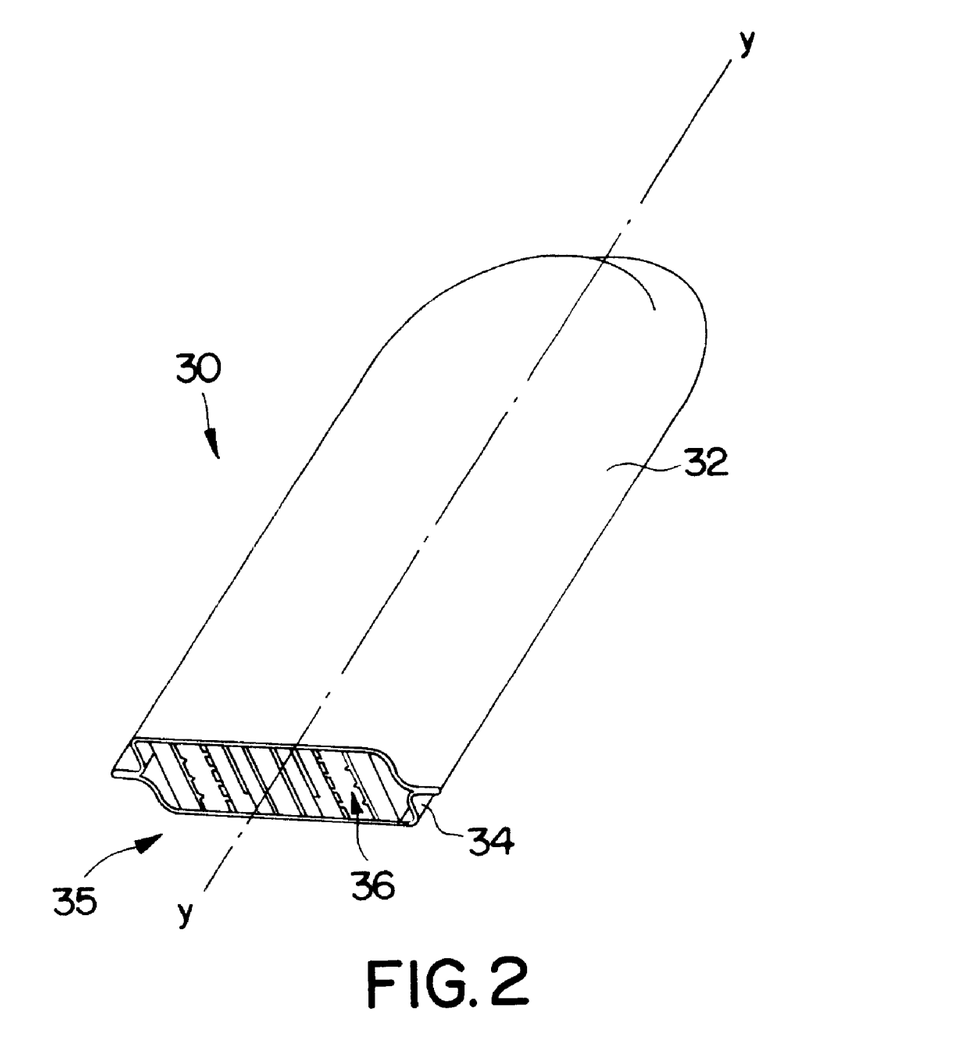
FIG. 2 is a partial sectional perspective view schematic of the absorbent article shown in FIG. 1.
Figure 3:
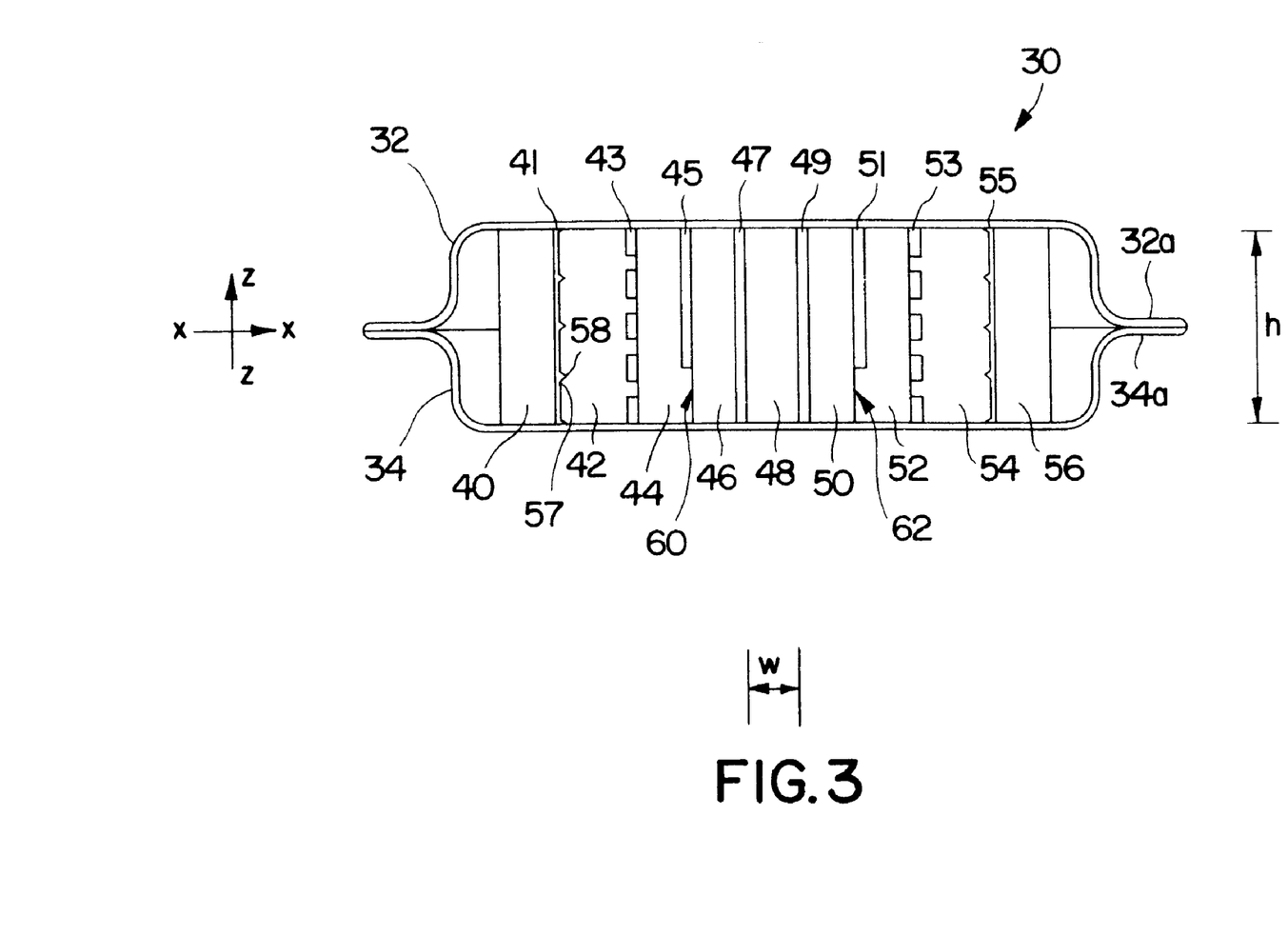
FIG. 3 is a simplified sectional side view schematic of the absorbent article shown in FIGS. 1 and 2.

Referring initially to FIGS. 1–3, there is illustrated an absorbent article, generally designated by the reference numeral 30, in accordance with one embodiment of the invention and which article is capable of absorbing body fluid. The absorbent article can be a diaper, training pant, sanitary napkin, panty liner, overnight pad, incontinence garment, underarm shield or other type of absorbent product capable of absorbing one or more bodily fluid such as urine, menses, blood, perspiration, excrement or the like. As will be appreciated, such an absorbent article will typically be disposable in nature. While the absorbent article 30 will be described herein in terms of a feminine care product such as a sanitary napkin, it is to be understood that the broader practice of the invention is not necessarily so limited and that the invention can, if desired be practiced in or in association with other types or forms of absorbent articles such as identified above.

The absorbent article 30 comprises a generally liquid pervious topsheet or cover 32 on the body-side surface of the article, a generally liquid impervious backsheet or baffle 34 on the opposing garment-facing side of the article and an absorbent core 35, disposed and enclosed therebetween.

It will be appreciated that absorbent articles such as feminine care products such as sanitary napkins may typically include additional standard or usual features such as relating to the positioning or placement of the article when in use. For example, certain sanitary napkin designs incorporate side flaps, sometimes referred to as "wings," such as can be helpful in preventing fluid flow from the sides of the napkin. Another example of such a feature is the inclusion or presence of an adhesive at or about the garment facing region face of the backsheet. Such adhesive surface of the article can be covered by a release paper or the like, as is known in the art, prior to use such as when in a packaged state. As such features are standard or common, are well known to those skilled in that art and form no part of the broader invention, they will not be shown or described in great detail herein.

The topsheet or cover 32 is generally designed to contact the body of the user and generally forms the contact surface of the absorbent article 30. In practice, the topsheet 32 can be constructed of a woven or nonwoven material, from synthetic or natural materials and desirably should be easily penetrated by body fluid. Suitable materials include bonded carded webs of polyester, polypropylene, polyethylene, nylon or other heat-bondable fibers. Other polyolefins, such as copolymers of polypropylene and polyethylene, linear low-density polyethylene, finely perforated film webs and net material also work well. The topsheet 32 may also be constructed of a thermoplastic film which contains apertures and is flanked on one or both sides by a nonwoven material.

Such an embodiment may desirably present a relatively soft feel against a user's thigh while allowing the rapid passage therethrough of body fluid.

The backsheet or baffle 34 is generally liquid impermeable and is designed to face the inner surface of an adjacent garment article, e.g., the crotch portion of an undergarment (not shown). The backsheet 34 may desirably be designed to permit the passage of air or vapor out of the absorbent article 30 while preventing or blocking the passage of fluids therethrough. As will be appreciated, the backsheet 34 can be made of any suitable material capable of providing or having the above-identified properties or characteristics. For example, suitable materials may include a microembossed polymeric film such as of polyethylene or polypropylene.

In general, the topsheet 32 and the backsheet 34 can be placed coextensive, in face-to-face contact around or about the absorbent core 35. Further, the topsheet 32 has a periphery 32a and the backsheet 34 has a periphery 34a which are desirably joined or sealed together by use of an adhesive, by heat sealing ultrasonics or other suitably selected techniques such as are known to those skilled in the art.

The absorbent core 35 is formed at least in part by an absorbent pad assembly 36. As shown in FIGS. 2 and 3, the absorbent pad assembly is a three-dimensional structure having a horizontal axis X—X, a vertical axis Z—Z and a length axis Y—Y. The absorbent pad assembly 36 includes a plurality of vertically orientated absorbent members 40, 42, 44, 46, 48, 50, 52, 54 and 56, respectively.

In practice, absorbent pad assemblies in accordance with the invention will typically include at least two and, preferably, at least three, such vertically orientated absorbent members. As will be appreciated, the specific number or nature of the absorbent members included within an absorbent pad assembly in accordance with the invention can generally be selected by one skilled in the art and guided by the teachings herein provided in order to satisfy the required or desired performance criteria of the particular application to which the assembly under consideration is directed. For example, absorbent members of the same or different material, construction, or absorbency characteristics or properties may be utilized for two or more, up to all the absorbent members making up a particular absorbent pad assembly in accordance with the invention. In general, however, in order to more fully realize the possible advantages attendant a multiple member absorbent pad assembly, absorbent pad assemblies in accordance with the invention will include at least two absorbent members different material, construction, or absorbency characteristics or properties.

As shown, a first generally planar fluid conveyance barrier member or fluid flow regulating wall 41 is interposed between the absorbent members 40 and 42. Similarly, a generally planar fluid conveyance barrier member or flow regulating wall 43 is interposed between the absorbent members 42 and 44. Further, generally planar fluid conveyance barrier members 45, 47, 49, 51, 53, and 55 are interposed between otherwise adjacent absorbent member pairs 44 and 46, 46 and 48, 48 and 50, 50 and 52, 52 and 54, as well as 54 and 56, respectively. As will be appreciated, the barrier members are each generally perpendicularly disposed relative to the contact surface of the absorbent article 30.

The barrier members (also sometimes referred to hereinafter as "flow regulating walls" or "fluid flow regulating walls") can take various forms and have a particular preselected permeability. Further, such barrier members may be incorporated in absorbent pad assemblies and absorbent articles in particular or specific arrangements such as to provide or result in particular or specific fluid flow control or management.

For example, one or more barrier members incorporated into an absorbent pad assembly and absorbent article in accordance with the invention may be semipermeable or impermeable to the fluid material to be controlled or regulated thereby, as may be specifically desired for or in particular applications or uses. Alternatively or in addition, one or more barrier members incorporated into a particular absorbent pad assembly and absorbent article in accordance with the invention may be in the form of a fluid flow directional material.

Barrier members for use in the practice of the invention can be fabricated or formed of various suitable materials of preselected permeability, such as are known in the art. Suitable impermeable barrier members can, dependent on the particular application, include coatings or films such as prevent the transmission of fluid therethrough. For example, such an impermeable coating or film can be applied to a suitable substrate such as to form an impermeable barrier member. Further suitable impermeable barrier members can, dependent on the particular application, include impermeable backsheet materials, such as described above, or non-absorbent foams, such as a closed cell, crosslinked or a non-crosslinked polyolefin foam, including, for example, polypropylene or a polyethylene foam. Examples of commercially available foams contemplated for such use in the present invention include the trade name CA-30 foam manufactured by Sealed Air Corp. of Fair Lawn, N.J. and trade name AF-030 foam manufactured by Astro-Valcour, Inc. of Glens Falls, N.Y.

Semipermeable barrier members can be composed of such materials which permit or allow the transmission of only certain fluids therethrough. For example, the inclusion of such semipermeable barrier members can serve to filter or screen fluids be transmitted therethrough. Suitable semipermeable barrier members can, dependent on the particular application, include porous or perforated film or net-like materials such as described in U.S. Pat. No. 4,616,644 to Saferstein et al. and U.S. Pat. No. 5,643,240 to Jackson et al., the disclosures of which are incorporated by reference herein in their entirety. For example, U.S. Pat. No. 4,616,644 discloses a series of light weight, nonwoven fabrics made from high-density polyethylene or polypropylene through a process of extrusion, embossing and orientation and referred to as Delnet film, available from Hercules Inc. and U.S. Pat. No. 5,643,240 discloses a suitable apertured film referred to as AET polyethylene CKX 215 film made by Applied Extrusion Technology of Middleton, Del.

Directional or flow directional barrier members can act like check valves to allow fluid to pass therethrough primarily in one direction. For example, an apertured film such as known for use as top or body-side surfaces in such absorbent articles can be used for such purposes.

Thus, barrier members used in the practice of the invention can be fabricated of various films, foams and the like. Further, in accordance with certain preferred embodiments of the invention, one or more of the barrier members may be in the form of such a film, foam or the like and which, is dissolvable after fluid contact such as to provide or result in a time release effect.

Thus, in the absorbent article 30 shown in FIGS. 1–3, the barrier members 45, 47, 49 and 51 are substantially fluid impermeable, such as prevent or avoid fluid flow therethrough. The barrier members 43 and 53 are semipermeable. That is, the semipermeable barrier member 43 permits selected fluid flow in the direction from the absorbent member 42 to the absorbent member 44 and vice versa. Similarly, the semipermeable barrier member 53 permits selected fluid flow in the direction from the absorbent member 52 to the absorbent member 54 and vice versa. In addition, the barrier members 41 and 55 are flow directional. That is, the barrier member 41 permits fluid flow in the direction from the absorbent member 40 to the absorbent member 42 but not vice versa. Similarly, the barrier member 55 permits fluid flow from the absorbent member 56 to the absorbent member 54 but not vice versa. In FIG. 3, the flow directional nature of the barrier members 41 and 55 is schematically signified by the cones 57 shown thereon. As shown, each of the cones 57 include an apex 58 pointed in the direction in which the flow is directed thereby. The use of fluid flow directional barrier members adjacent or otherwise near one or more of the terminal absorbent members of a particular absorbent pad assembly can be helpful in better ensuring either or both avoidance of fluid overflow over the edge of the pad assembly and increased utilization of the existing absorbency within the pad assembly. However, it is to be understood that numerous various particular arrangements of barrier and absorbent members in accordance with the invention are possible and the broader practice of the invention is not generally limited to a specific or particular such arrangement. For example, one or more such fluid flow directional barrier members can, if desired, be positioned and orientated such as to direct flow toward an edge, rather than the center, of the respective absorbent pad assembly.

Further, one or more barrier members in accordance with the invention may be vertically coextensive with adjacent associated absorbent members, such as shown by the barrier members 41, 43, 47, 49, 53, and 55. Alternatively or in addition, one or more barrier members in accordance with the invention may be vertically non-coextensive with adjacent absorbent members, such as shown by the barrier member 45 relative to adjacent absorbent members 44 and 46, respectively, and barrier member 51 relative to adjacent absorbent members 50 and 52, respectively. Thus, adjacent absorbent member 44 and 46 form a surface interface 60 therebetween and adjacent absorbent members 50 and 52 form a surface interface 62. In the preferred illustrated embodiment, the surface interfaces 60 and 62 are generally positioned at the side of the absorbent article 30 opposite the contact surface shown by the cover 32, e.g., adjacent or near the backsheet 34. It is to be understood, however, that the broader practice of the invention is not necessarily so limited.

The surface interfaces 60 and 62 permit fluid to be transferred or communicated from the one adjacent absorbent member to the other. As will be appreciated, such structure or arrangement can serve to facilitate the more complete utilization of the absorbent capacity of a particular absorbent pad assembly. For example, in accordance with certain preferred embodiments of the invention, fluid would generally communicate across such surface interface only after the absorbent capacity of one or the other of the adjacent absorbent members has been significantly utilized.

As shown, the otherwise adjacent absorbent members are horizontally displaced relative to each other along the entire vertical heights thereof. That is, such otherwise adjacent absorbent members generally do not have any portions having the same placement on the X—X axis. For example, no portion of absorbent member 40 underlies or has the same X—X axis placement as a portion of adjacent absorbent member 42.

Each of the absorbent members 40, 42, 44, 46, 48, 50 and 52 is generally planar and perpendicularly disposed relative to the contact surface of the absorbent article 30. The absorbent members each have a vertical height (h), a horizontal width (w) and a longitudinal length (l). As will be appreciated, the specific height, width and length of the absorbent members used will generally be selected to satisfy the particular requirement of the application to which such absorbent members are to be applied. Absorbent members used in the practice of the invention will generally have a width of in the range of about 0.03 mm to no more than about 20 mm and a height of about 1 mm to about 15 mm. In practice, however, absorbent members used in the invention will typically have a width of no more than about 8 mm (e.g., in the range of about 0.5 mm to about 8 mm) and, preferably, will have a width of no more than about 5 mm (e.g., in the range of about 1 mm to about 5 mm).

In addition, one or more of the vertical height, horizontal width and longitudinal length of a particular absorbent member may be the same or different from that of other absorbent member or members of a particular pad assembly. For example, as shown in FIG. 1, side disposed absorbent member 56 is of shorter length (l) than centrally placed absorbent members such as absorbent members 46, 48 and 50. Also, as shown in FIG. 3, absorbent member 42 is of greater width (w) than absorbent member 44, for example. Similarly, while FIG. 3 shows each of the absorbent members as having substantially the same vertical height (h) and while such use may facilitate manufacture and assembly and thus be generally preferred, absorbent members having different or otherwise selected vertical heights can be used.

In accordance with certain preferred embodiments of the invention, one or more of the vertical height, horizontal width and longitudinal length of a particular absorbent member may be varying or constant and uniform for the entire absorbent member, as may be desired in a particular application. Further, in those absorbent members wherein one or more of the vertical height, horizontal width and longitudinal length varies, such variation may be continuous or in one or more steps. Still further, such variation, if present, may be uniform or not, as may be desired.

In accordance with the invention, the absorbent members are advantageously arranged such as to generally provide a much lower width to height ratio than normally obtained or realized in absorbent articles such as sanitary napkins. Such an absorbent member arrangements, with a significantly lower width to height ratios, promote wicking in the directions of the Y—Y and Z—Z axis since fluid is more likely to travel to fibers in close proximity rather than span across vertically disposed surface interfaces formed between the adjacent absorbent members.

Further, the vertical orientation of adjacent absorbent members in accordance with the invention permits the design of absorbent pad assemblies and associated absorbent articles which facilitate the use of selected and multiple absorbent materials in close proximity to the fluid intake area. As will be appreciated by those skilled in the art, at least certain absorbent articles, including various feminine care products such as including sanitary napkins, may be required to satisfactorily perform in association with fluids having variable or a wide range of possible or likely constituents. Thus, the subject invention development of absorbent pad assemblies and absorbent articles wherein possible multiple different absorbent materials can be conveniently placed in close proximity to the fluid intake area is a significant advancement in the art. Also, the absorbent pad assemblies and absorbent articles of the invention can advantageously avoid complications such as relating to horizontal dependency, such as described above.

In accordance with one preferred embodiment of the invention, absorbent members preferably have a width to height ratio of less than 1 in order to more fully realize the benefits of the specifically orientated absorbent members of the subject absorbent pad assembly and absorbent article.

While the height and width of each of the absorbent members for the absorbent pad assembly 36 are the same, it is to be understood that the broader practice of the invention is not necessarily so limited and that the invention can, if desired, be practiced in conjunction with absorbent members which differ in height, width or both.

Absorbent members for use in the practice of the invention can be fabricated or formed of various suitable absorbent materials such as are known in the art. For example, selected absorbent members for use in the practice of the invention can be fabricated or formed of various hydrophilic types of natural or synthetic fibers including cellulose fibers, surfactant-treated meltblown fibers, wood pulp fibers, regenerated cellulose, cotton fibers or a blend of other fibers.

Absorbent member materials of construction can include a material described in U.S. Pat. No. 4,100,324 and generally known as coform. Coform is available from the Kimberly-Clark Corporation located in Neenah, Wis. and is generally a nonwoven material made up of an airform matrix of thermoplastic polymeric fibers and a multiplicity of individualized wood pulp fibers, and has a fabric-like finish. The thermoplastic fiber polymers generally have an average diameter of less than 10 microns with the individualized wood pulp fibers dispersed throughout the matrix and serving to space these microfibers from each other. Such material can be formed by initially utilizing the primary air stream with the meltblown microfibers and the secondary air stream containing wood pulp fibers and merging the two streams under turbulent conditions to form an integrated air stream along a forming surface.

In certain embodiments, the use of absorbent materials in the nature of surge materials may be desired. Various woven fabrics and nonwoven webs can be used to construct surge materials. For example, a surge material may be a nonwoven fabric layer composed of a meltblown or spunbond web of polyolefin filaments. Such nonwoven fabric layers may include conjugate, biconstituent and homopolymer fibers of staple or other lengths and mixtures of such fibers with other types of fibers. The surge material also can be a bonded carded web or an airlaid web composed of natural and/or synthetic fibers. The bonded carded web may, for example, be a powder bonded carded web, an infrared bonded carded web, or a through-air bonded carded web. The bonded carded webs can optionally include a mixture or blend of different fibers, and the fiber lengths within a selected web may range from about 3 mm to about 60 mm.

Examples of particular surge materials may be found in U.S. Pat. No. 5,490,846 to Ellis et al. and in U.S. Pat. No. 5,364,382 to Latimer. Surge materials may be composed of a substantially hydrophobic material, and the hydrophobic material may optionally be treated with a surfactant or otherwise processed to impart a desired level of wettability and hydrophilicity.

Another possible suitable absorbent material is the material known as PRISM available from Kimberly-Clark Corporation. A description of PRISM is taught in U.S. Pat. No. 5,336,552 to Strack et al. and the disclosure of that patent is incorporated by reference herein in its entirety. PRISM is generally the nonwoven fabric and comprises extruded multicomponent polymeric strands including first and second polymeric components arranged in substantially distinctive zones across the cross-section of the multicomponent strands and extending continuously along the length of the multicomponent strands. Preferably, the strands are continuous filaments which may be formed by spunbonding techniques. The second component of the strands constitutes at least a portion of the peripheral surface of the multicomponent strands continuously along the length of the multicomponent strands and includes a blend of a polyolefin and an ethylene alkyl acrylate copolymer. Bonds between the multicomponent strands may be formed by the application of heat. More specifically, the first polymeric component of the multicomponent strands is present in an amount of from about 20 to about 80 percent by weight of the strands and the second polymeric component is present in an amount from about 80 to about 20 percent by weight of the strands. Preferably, the first polymeric component of the multicomponent strands is present in an amount of from about 40 to about 60 percent by weight of the strands and the second polymeric component is present in an amount from about 60 to about 40 percent by weight of the strands.

The term "strand" as used herein refers to an elongated extrudate formed by passing a polymer through a forming orifice such a die. Strands include fibers, which are discontinuous strands having a definite length, and filaments, which are continuous strands of material. The nonwoven fabric of the present invention may be formed from staple multicomponent fibers. Such staple fibers may be carded and bonded to form the nonwoven fabric. Preferably, however, the nonwoven fabric of the present invention is made with continuous spunbond multicomponent filaments which are extruded, drawn and laid on a traveling forming surface.

The types of nonwoven materials that may be employed include powder-bonded-carded webs, infrared bonded carded webs, and through-air-bonded-carded webs. The infrared and through-air bonded carded webs can optionally include a mixture of different fibers, and the fiber lengths within a selected fabric web may be within the range of about 1.0 to 3.0 inch and an average bulk density of about 0.02 g/cc to about 0.12 g/cc.

Other suitable absorbent materials for use in the practice of the invention can include materials commonly referred to as superabsorbents. Superabsorbents can be in various forms including particulate and fibrous forms. Known superabsorbent materials include AFA-130-53C by Dow Chemical, and W77553 and FAV880A which are commercially available from the Stockhausen Company of Greensboro, N.C. Stockhausen's W77553 is a bulk polymerized polyacrylate with a hydrophobic surface treatment. Stockhausen's FAV880A is a highly crosslinked surface superabsorbent. AFA 130-53C is a 850 to 1400 micron suspension polymerized polyacrylate material available from The Dow Chemical Company of Midland, Mich.

Hydrocolloidal materials, commonly referred to as superabsorbents, can be in the form of a hydrogel-forming polymer composition which is water-insoluble, slightly cross-linked, and partially neutralized. It can be prepared from an unsaturated polymerizable, acid group-containing monomers and cross-linked agents. Such superabsorbents are taught in U.S. Pat. No. 4,798,603 to Meyers et al., U.S. Reissue Patent 32,649 to Brandt et al. and U.S. Pat. No. 4,467,012 to Pedersen et al., as well as in published European Patent Application 0,339,461 to Kellenberger. The disclosures of these patents and the European Patent Application are incorporated by reference herein in their entirety.

Additionally, materials known as "slow rate" superabsorbents can also be used in the practice of the subject invention. By "slow rate" superabsorbent what is meant is a superabsorbent having an absorption time index (ATI) of at least 5 minutes and preferably more than 10 minutes. Adjusting the rate of absorbency of a superabsorbent may be achieved by modifications to the particle size, surface properties, and chemistry of the polymer. Such slow rate superabsorbents are described in greater detail in U.S. Pat. No. 5,843,063 to Anderson et al., the disclosure of which patent is incorporated herein its entirety.

Suitable absorbent materials for use in the practice of the invention may also take the form of absorbent foams such as open cell polyurethane foam, such as disclosed in U.S. Pat. No. 5,853,402 to Faulks et al., the disclosure of which patent is incorporated herein its entirety. Further, starch foams such as disclosed in U.S. Pat. No. 5,506,277 to Griesbach III, the disclosure of which patent is incorporated herein its entirety, may also be used.

The invention may also utilize, as suitable absorbent materials, corrugated nonwoven fabrics such as the high bulk corrugated nonwoven fabric disclosed in U.S. Pat. No. 3,668,054 to Stumpf, the disclosure of which patent is incorporated herein its entirety. As disclosed therein, such fabric generally comprises a corrugated web of initially aligned textile fibers implanted in a continuous thin film of a thermoplastic adhesive having an essentially constant thickness. The resulting web-adhesive material is then corrugated to provide the multitude of furrows and grooves, which are irregularly connected near their roots and along their respective sides.

As will be appreciated, appropriate materials for use in the practice of the invention can be variously suitably formed including being meltblown or airlaid or airformed. The term "meltblown fibers" generally refers to fibers formed by extruding a molten thermoplastic material through a plurality of fine, usually circular, die capillaries as molten threads or filaments and into converging high velocity gas (e.g., air) streams which attenuate the filaments of molten thermoplastic material to reduce their diameters. Thereafter, the meltblown fibers are typically carried by the high velocity gas stream and deposited on a collecting surface to form a web of randomly disbursed meltblown fibers. Meltblown fibers may be continuous or discontinuous and are generally tacky when deposited onto a collecting surface. Meltblown materials are described in greater detail in U.S. Pat. No. 5,656,361 to Vogt et al., the disclosure of which is fully incorporated herein by reference.

Further, absorbent member materials of construction which contain or include one or more of various additives such as coagulants, lysing agent or superabsorbents, for example, can also be used. As identified above, adjacent absorbent members will preferably differ in one or more property or characteristic such as chemical composition or construction such as fiber orientation or thickness, for example. In accordance with one preferred embodiment of the invention, such adjacent absorbent members advantageously preferably differ in a selected property or characteristic other than density and such as not easily obtainable with prior art techniques. In particular, the minimization or elimination of horizontal dependency by or between adjacent absorbent layers can result in the utilization of absorbent materials selected for special or particular properties or characteristic.

Moreover, it is to be understood that the broader practice of the invention is not necessarily limited to specific or particular absorbent materials and that other absorbent materials such as are known to those skilled in the art can, if desired, be used. For example, a wide assortment of materials have been designed and developed to better handle or address the various conditions to which such products may be required to perform.

In the practice of the invention, barrier members and absorbent members can be loosely plied or bonded to adjacent barrier members and absorbent members, as may be desired, such as via the use of adhesives, thermal or ultrasonic techniques, threading or sewing techniques or other suitable joining technique such as known in the art.

It is be understood that the broader practice of the invention is not necessarily limited to the incorporation of absorbent pad assemblies, such as described above, as the whole or substantially entire absorbent core. For example, absorbent articles in accordance with the invention can incorporate such absorbent pad assemblies as a portion of the absorbent core with other absorbent elements, including possibly other absorbent materials, plied, folded or otherwise formed adjacent thereto.

Further, absorbent articles in accordance with the invention can include a central portion which is formed by or includes other absorbent elements with an absorbent pad assembly in accordance with the invention plied, folded or otherwise formed adjacent thereto.

Figure 4:
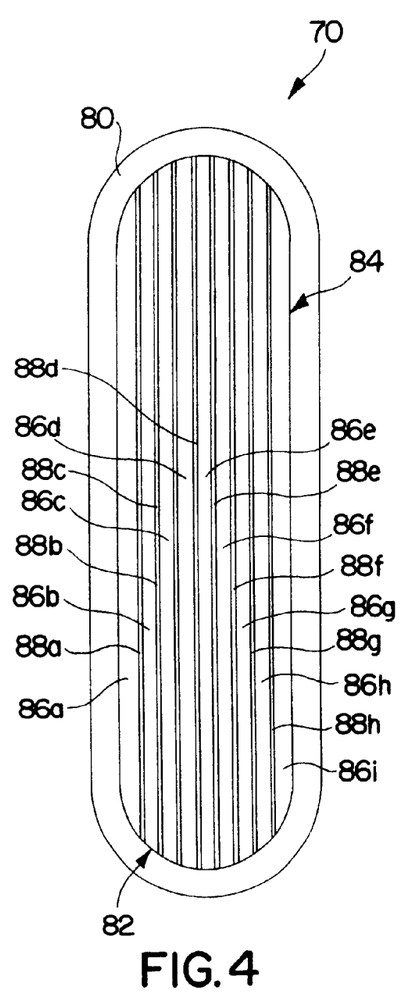
FIGS. 4–6 are simplified fragmentary top view schematics of absorbent articles in accordance with alternative embodiments of the invention.
Figure 5:
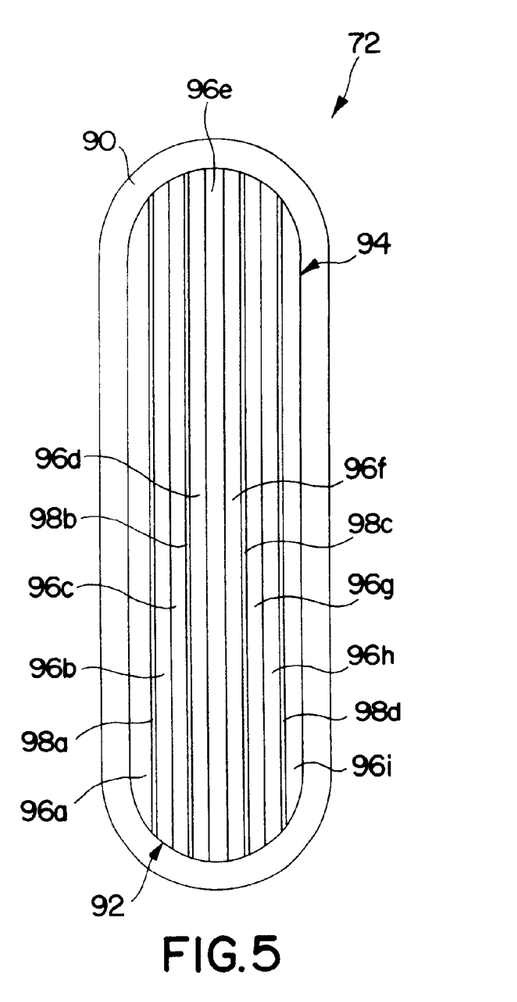
Figure 6:
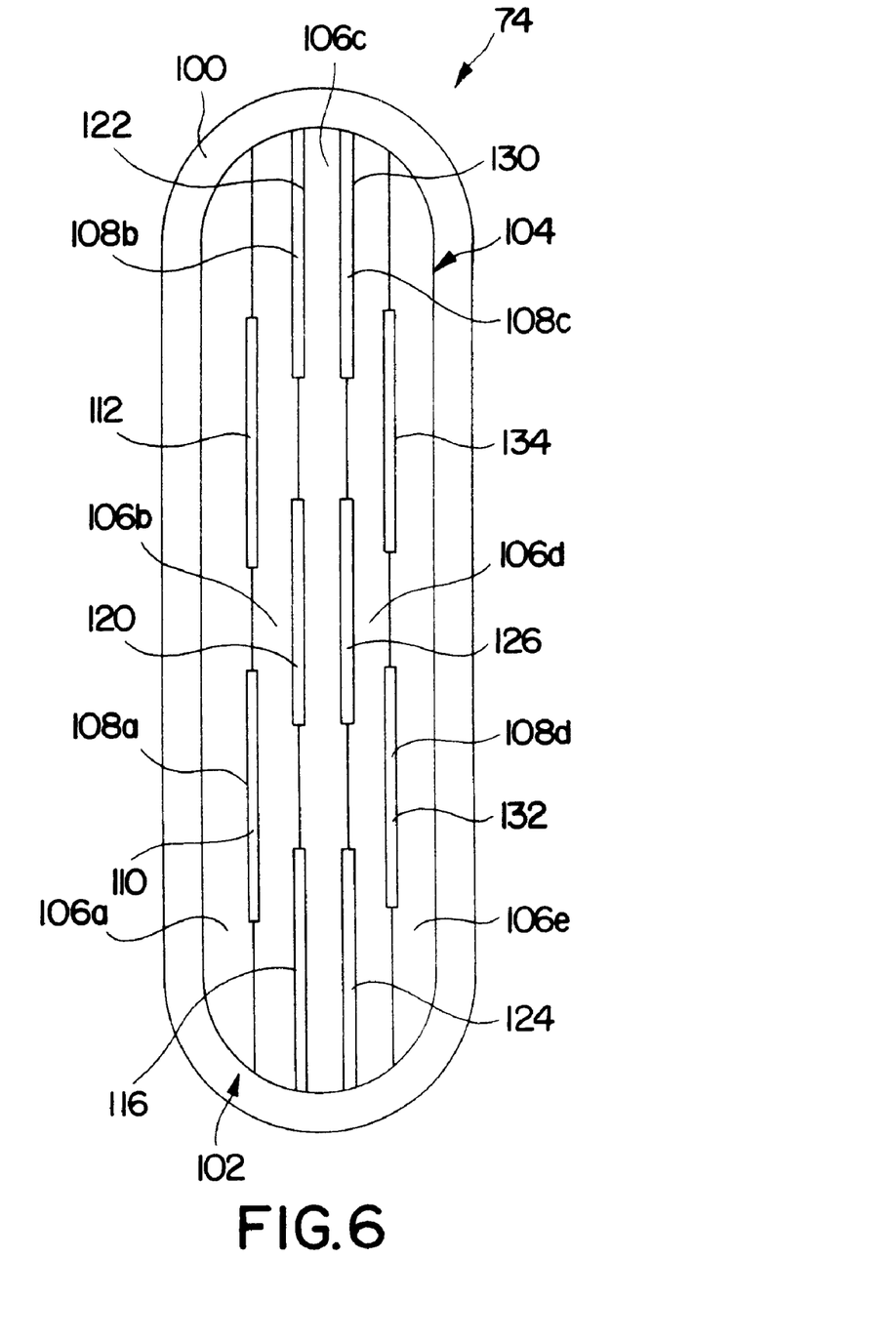

FIGS. 4–6 are simplified fragmentary top view schematics of absorbent articles 70, 72, and 74, respectively, in accordance with alternative embodiments of the invention.

As shown in FIG. 4, the absorbent article 70 includes a backsheet 80, an absorbent core 82 and a topsheet (not shown). The absorbent core 82 includes a centrally positioned or placed absorbent pad assembly 84, similar to that described above with a plurality of vertically orientated absorbent members 86(a–i), respectively, with generally planar fluid conveyance barrier members 88(a–h) interposed between respective otherwise adjacent absorbent member pairs.

FIG. 5 illustrates the absorbent article 72 which includes a backsheet 90, an absorbent core 92, and a topsheet (not shown). The absorbent core 92 includes a centrally positioned or placed absorbent pad assembly 94, similar to that described above, however, with 2 or more absorbent members interposed between at least certain of the most adjacent of the barrier members.

More specifically, the absorbent pad assembly 94 includes a plurality of vertically orientated absorbent members 96(a–i), respectively, with generally planar fluid conveyance barrier members 98(a–d).

FIG. 6 illustrates the absorbent article 74 which includes a backsheet 100, an absorbent core 102, and a topsheet (not shown). The absorbent core 102 includes a centrally positioned or placed absorbent pad assembly 104, similar to those described above with a plurality of vertically orientated absorbent members 106(a–e), respectively, and generally planar fluid conveyance barrier members 108(a–d). In the absorbent pad assembly 104, however, one or more of the generally planar fluid conveyance barrier members 108 (a–d) is in or of intermittent form. For example, the conveyance barrier member 108a include a first segment 110 and a second segment 112. Similarly the conveyance barrier member 108b includes segments 116, 120, and 122; the conveyance barrier member 108c includes segments 124, 126, and 130; and the conveyance barrier member 108d includes segments 132 and 134.

While the barrier member segments and absorbent members of the absorbent article 74 are shown as having a uniform or symmetrical pattern, the broader practice of the invention is not necessarily so limited. For example, either or both barrier member segments and absorbent members can be in non-uniform or non-symmetric pattern, in accordance with the needs of the specific application to which the absorbent pad assembly or absorbent article is to be applied.

While the segments for a particular barrier member need not necessarily be joined together, the use of joined together barrier member segments will generally simplify manufacture and assembly and is thus generally preferred. However, the use of segments which are not joined together may permit greater design flexibility as, for example, two or more different materials can be used for each of the segments of a particular barrier member.

Figure 7:
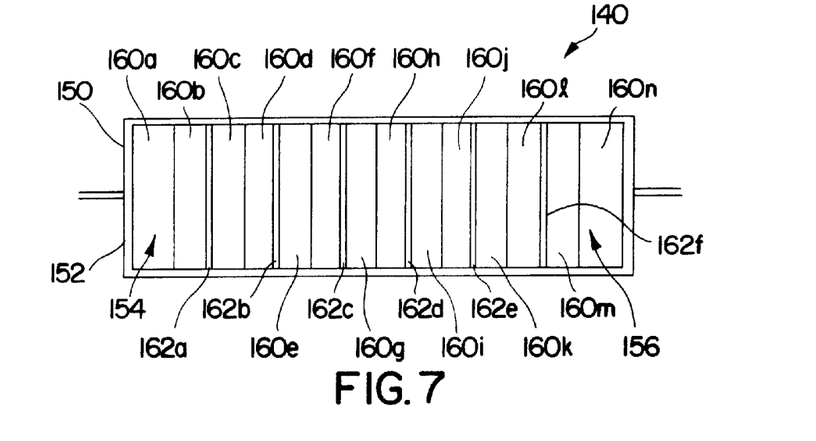
FIGS. 7–9 are simplified sectional side view schematics of absorbent articles, as viewed along the X—X axis, in accordance with alternative embodiments of the invention.
Figure 8:
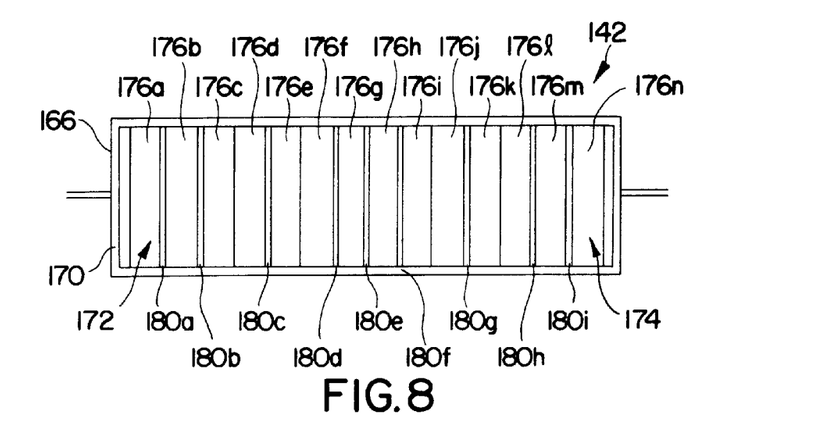
Figure 9:
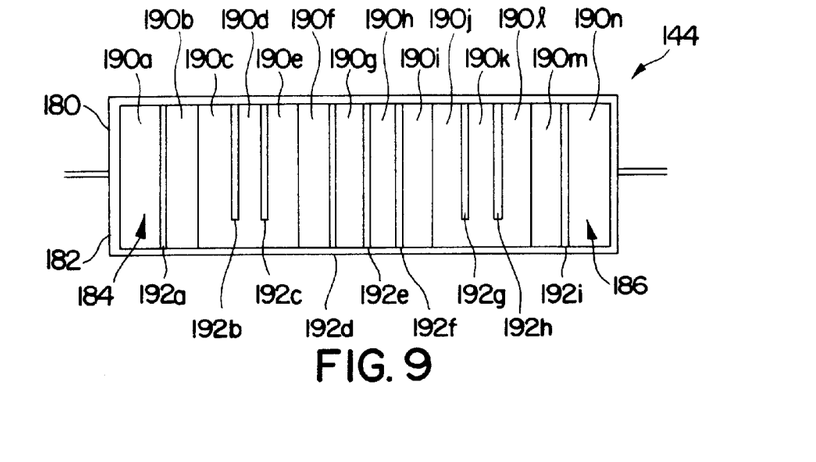

FIGS. 7–9 are simplified sectional side view schematics of absorbent articles 140, 142, and 144, respectively, in accordance with certain alternative preferred embodiments of the invention, and viewed in the direction of the X—X axis.

FIG. 7 illustrates the absorbent article 140 which includes a topsheet 150 and a backsheet 152, such as described above, and an absorbent core 154. The absorbent core 154 includes an absorbent pad assembly 156, in accordance with one embodiment of the invention. More specifically, the absorbent pad assembly 156 is generally composed of a plurality of vertically orientated absorbent members 160($a$–$m$), respectively, and generally planar fluid conveyance barrier members 162($a$–$f$).

FIG. 8 illustrates the absorbent article 142 which includes a topsheet 166 and a backsheet 170, such as described above, and an absorbent core 172. The absorbent core 172 includes an absorbent pad assembly 174 in accordance with one particular embodiment of the invention and such as composed of a plurality of vertically orientated absorbent members 176($a$–$n$), respectively, and generally planar fluid conveyance barrier members 180($a$–$i$), in an arrangement in accordance with one preferred embodiment of the invention. In these and subsequent drawings, the semipermeable or directional nature of certain of such barrier members, is simply shown through the reference characters assigned thereto and identified herein, rather than through the use of cones and the like such as used in relation to FIG. 3, discussed above.

In accordance with such embodiment, the barrier members 180$c$ and 180$g$ are generally impermeable to fluid flow therethrough, the barrier members 180$d$, 180$e$ and 180$f$ are semipermeable in nature and as such do not generally permit the flow therethrough of at least certain materials, and the barrier members 180$a$, 180$b$, 180$h$ and 180$i$ are directional barriers such that fluid will generally preferably flow therethrough in a particular direction. More specifically, the barrier member 180$a$ generally only permits fluid flow therethrough from the direction of the absorbent member 176$a$ to the absorbent member 176$b$. Similarly, the barrier members 180$b$, 180$h$ and 180$i$ generally only permit fluid flow therethrough in the direction of the absorbent member 176$b$ to the absorbent member 176$c$, in the direction of the absorbent member 176$m$ to the absorbent member 176$l$, and the absorbent member 176$n$ to the absorbent member 176$m$, respectively.

As will be apparent to those skilled in the art, such or similar designs or arrangements can be used such as to desirably provide and absorbent pad assembly or associated absorbent article having particularly desired or sought absorbency properties or characteristics, such as may be more particularly suited for specific applications or uses.

FIG. 9 illustrates the absorbent article 144 which includes a topsheet 180 and a backsheet 182, such as described above, and an absorbent core 184. The absorbent core 184 includes an absorbent pad assembly 186 in accordance with one particular embodiment of the invention and such as composed of a plurality of vertically orientated absorbent members 190($a$–$n$), respectively, and generally planar fluid conveyance barrier members 192($a$–$i$), in an arrangement in accordance with another preferred embodiment of the invention.

In the absorbent article 144, the barrier members 192$b$, 192$c$, 192$g$ and 192$h$ are each vertically non-coextensive with adjacent absorbent members such as desired above relative to the absorbent article 30 and as shown in FIG. 3 and such as may permit contact between selected portions of adjacent absorbent members.

It is to be understood that various modifications and combinations of the above-described embodiments are possible and are herein encompassed. For example, such possible modifications of the various above-described embodiments can involve the inclusion of one or more overlying or underlying void layer or layer of other selected absorbent article material. More particularly, it may be desirable to include within an absorbent article, in accordance with the invention, a layer of a fluid retention material underlying an absorbent pad assembly, such as described above. In some applications it may be desirable to include a layer of fluid surge material, such as is known in the art, in overlying relation to an absorbent pad assembly, such as described above. Further, the extent of such overlying or underlying, as the case may be, of each such overlying or underlying layer can be partial or complete, as may be desired for a particular application.

Absorbent structures, in accordance with the invention, can be conveniently formed or made by adjacently disposing a first generally planar fluid conveyance barrier member of preselected permeability, such as described above, between selected absorbent members, such as also described above, and orientating the adjacently disposed barrier member and absorbent members to provide or otherwise result in a structure having a desired ratio of horizontal width to vertical height. As detailed above, structures in accordance with the invention advantageously include absorbent members having a ratio of horizontal width to vertical height of no more than about 10:1, preferably no more than about 5:1 and, more preferably about 1:1 or less. It is to be understood that the forming or making of such structures may involve the desired selection of one or more desired variables or parameters, such as described above, including: the number, size and shape of either or both adjacently disposed barrier and absorbent members as well as the properties, characteristics and materials of construction of either or both such barrier and absorbent members, for example, and such as guided by the teachings herein provided.

As will be appreciated, either or both the barrier and absorbent members may be initially provided in various orientations such as may or may not require subsequent reorientation. In one particular formation method in accordance with the invention, however, barrier and absorbent members are horizontally layered and subsequently vertically reorientated to provide the desired structure.

As described above, adjacent barrier and absorbent members can, if desired, be loosely plied or, if desired, bonded to one another such as via the use of adhesives, thermal or ultrasonic techniques, threading or sewing techniques or other suitable joining technique such as known in the art. In accordance with one preferred practice of the invention, such bonding, if used, is preferably done prior to any reorientation, that may be required.

Further, methods for forming such absorbent structures in accordance with the invention may include one or more cutting steps or operations. For example, adjacently disposed barrier and absorbent members may be appropriately cut to provide or supply an absorbent pad assembly in a desired selected shape or form such as suitable for the specific use to which such absorbent pad assembly is intended to be applied. Such cutting may occur prior, after or both prior and after orientation as may be desired in specific applications. Various means, such as known in the art, are available whereby such cutting of the adjacently disposed barrier and absorbent members can be accomplished including, slit blade and water jet cutting, for example.

While the invention has been described above relative to absorbent articles wherein the absorbent core contains a single absorbent pad assembly in accordance with the invention, it is to be understood that the broader practice of the invention is not necessarily so limited. For example, as will be appreciated by those skilled in the art, the invention can, if desired, be practiced with absorbent articles containing two or other selected multiple of such absorbent pad assemblies. Further, such absorbent articles may contain such two or more absorbent pad assemblies in spaced apart, overlying, partially overlapping or other selected relationship, as may be desired for a particular application.

Thus, the invention provides absorbent pad assemblies, absorbent articles and associated methods which permit the more complete or full utilization of the absorbent capacity thereof as may be desired. For example, absorbent pad assemblies and absorbent articles, can have barrier members, such as described above, situated between selected vertical segments of particular absorbent members to regulate fluid flow therein. In particular, such absorbent pad assemblies and absorbent articles can be orientated and designed such that the barrier members serve to direct fluid flow such as to permit better utilization of the absorbent capacity such as through better or more complete unitization of the center portion and length of the respective absorbent article while generally avoiding undesired saturation of the edges of the absorbent article with fluid such as by preferentially draining or directing fluid flow toward the center of the absorbent structure. In view of the above, it will be appreciated that the invention also generally provides absorbent pad assemblies, absorbent articles and associated methods which can respond to the possibly wide range of operating and performance conditions to which such assemblies and articles can be exposed in either or both a more effective and efficient manner than previously otherwise attainable.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

I claim:

1. A method comprising:
   adjacently disposing at least a first generally planar fluid conveyance barrier member of preselected permeability between at least first and second absorbent members, and
   orientating the adjacently disposed barrier member and first and second absorbent members wherein each of the first and second absorbent members has a ratio of horizontal width to vertical height of no more than about 10:1.

2. The method of claim 1 wherein the orientated adjacently disposed first and second absorbent members each have a ratio of horizontal width to vertical height of no more than about 1:1.

3. The method of claim 1 additionally comprising:
   cutting the adjacently disposed first barrier member and first and second absorbent members to form an absorbent pad assembly.

4. The method of claim 3 wherein the adjacently disposed first barrier member and first and second absorbent members are cut prior to the orientation.

5. The method of claim 3 wherein the adjacently disposed first barrier member and first and second absorbent members are cut following the orientation.

6. The method of claim 3 wherein the cutting step comprises slit blade cutting.

7. The method of claim 3 wherein the cutting step comprises water jet cutting.

8. The method of claim 1 additionally comprising the step of bonding the adjacently disposed first barrier member with at least one of the first and second absorbent members prior to the orientation.

9. The method of claim 8 wherein the bonding step comprises adhesive bonding.

10. The method of claim 8 wherein the bonding step comprises thermal bonding.

11. The method of claim 8 wherein the bonding step comprises ultrasonic bonding.

12. The method of claim 8 wherein the first barrier member is bonded to each of the first and second absorbent members prior to the orientation.

13. The method of claim 1 wherein the first barrier member comprises an impermeable material.

14. The method of claim 1 wherein the first barrier member comprises a flow directional material.

15. The method of claim 1 wherein the first barrier member comprises a semipermeable material.

16. The method of claim 1 wherein the first barrier member and at least one of the first and second absorbent members are vertically coextensive.

17. The method of claim 16 wherein the first barrier member and both the first and second absorbent members are vertically coextensive.

18. The method of claim 1 wherein the first barrier member and at least one of the first and second absorbent members are vertically non-coextensive.

19. The method of claim 18 wherein the first barrier member and both the first and second absorbent members are vertically non-coextensive.

20. The method of claim 1 wherein the first barrier member is of intermittent form.

21. The method of claim 1 wherein the first and second absorbent members are each formed of materials of different absorbency.

22. The method of claim 1 wherein the first and second absorbent members are each formed of materials having similar absorbency.

23. The method of claim 1 additionally comprising a second barrier member spaced apart from the first barrier member by at least the second absorbent member.

24. The method of claim 23 wherein the first and second barrier members are spaced apart by at least one absorbent member in addition to the second absorbent member.

25. A method for forming an absorbent pad assembly, said method comprising:
   horizontally layering at least a first generally planar fluid conveyance barrier member of preselected permeability between first and second absorbent members and
   vertically reorientating the horizontally layered barrier member and first and second absorbent members.

26. The method of claim 25 additionally comprising:
   cutting the horizontally layered first conveyance barrier member and first and second absorbent members.

27. The method of claim 25 additionally comprising the step of bonding the horizontally layered first conveyance barrier member to the first and second absorbent members, respectively, prior to the vertical reorientation.

28. The method of claim 25 wherein the vertically reorientated first and second absorbent members each have a width of no more than about 20 mm.

29. The method of claim 25 wherein the vertically reorientated first and second absorbent members each have a width to height ratio of less than 1.

* * * * *